US00PP10175P

United States Patent [19]

Zaiger et al.

[11] Patent Number: Plant 10,175

[45] Date of Patent: Jan. 6, 1998

[54] PEACH TREE 'SNOW BEAUTY'

[76] Inventors: Chris Floyd Zaiger, 929 Grimes Ave.; Gary Neil Zaiger, 1908 Elm Ave.; Leith Marie Gardner, 1207 Grimes Ave.; Grant Gene Zaiger, 4005 Caliifornia Ave., all of Modesto, Calif. 95358

[21] Appl. No.: 706,191

[22] Filed: Aug. 30, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

The new and distinct variety of peach *Prunus persica tree has the following combination of unique and desirable features:*

1. Heavy and regular bearer of large size fruit.
2. Fruit with excellent flavor and eating quality.
3. Fruit with firm, white flesh, good handling and shipping quality.
4. Fruit with an attractive red skin color.
5. Fruit staying firm on the tree 6 to 7 days after maturity (shipping ripe).
6. Vigorous, upright growth of the tree.

1 Drawing Sheet

ORIGIN OF THE VARIETY

The present new variety of peach tree was developed by us in our experimental orchard located near Modesto, Calif., as a first generation cross between two selected seedlings with the field identification numbers 30EB280 and 1GC131. The maternal parent, field identification number 30EB280, originated from a first generation cross of two selected seedlings. One originated from a cross of Redwing Peach (U.S. Plant Pat. No. 621) with a nectarine of unknown parentage. The other originated from a cross of Fayette Peach (non-patented) with May Grand Nectarine (U.S. Plant Pat. No. 2794). The paternal parent, field identification number 1GC131, also originated from a cross between two selected seedlings. One seedling originated from a cross of Fayette Peach (non-patented) with a low chilling non-melting clingstone peach of unknown parentage. The other originated from an open pollinated May Grand Nectarine (U.S. Plant Pat. No. 2794) seedling.

ASEXUAL REPRODUCTION OF THE VARIETY

Asexual reproduction of the present new variety by budding was performed by us in our experimental orchard located near Modesto, Calif., and shows that all characteristics are established and transmitted through succeeding asexual propagations and run true to the original tree in all respects.

SUMMARY OF THE NEW VARIETY

The present new and distinct variety of peach tree is of large size, vigorous, upright growth, a productive and regular bearer of large, white flesh, freestone fruit, substantially overspread with an attractive red skin color. The fruit is further characterized by being sub-acid, mild and sweet with excellent flavor and eating quality, having firm flesh with good handling and shipping quality, staying firm on the tree 6 to 7 days after maturity (shipping ripe) and maturing approximately 10 days after White Lady Peach (U.S. Plant Pat. No. 5821).

PHOTOGRAPH OF THE VARIETY

The accompanying color photograph show typical specimens of the foliage and fruit of the present new peach variety, the upper and lower surface of the leaves being illustrated, an exterior and a cross sectional view of a fruit divided in the suture plane to reveal flesh coloration, pit cavity and a stone remaining In place. The photographic illustration was taken shortly after being picked at maturity (firm ripe) and the colors are as nearly true as is reasonably possible in a color presentation of this type.

DESCRIPTION OF THE VARIETY

The botanical details of the new and distinct variety of peach tree, its flowers, foliage and fruit are based on observations of specimens grown near Modesto, Calif., with color terminology (except those in common terms) referenced to Reinhold Color Atlas by A. Kornerup and H. Wanscher.

Tree:
- *Size.*—Large.
- *Vigor.*—Vigorous.
- *Form.*—Upright.
- *Density.*—Medium dense.
- *Productivity.*—Productive.
- *Bearer.*—Regular.
- *Shape.*—Normally pruned to vase shape.

Trunk:
- *Size.*—Large.
- *Surface.*—Medium shaggy.
- *Color.*—Brown to grayish brown (5-E-4) to (5-E-5).

Branches:
- *Size.*—Medium.
- *Surface.*—Smooth to medium rough.
- *Lenticels.*—Numerous. Medium to large in size.
- *Color.*—Dark blond to oak brown (5-D-4) to (5-D-6). Varies with age of growth.

Leaves:
- *Size.*—Large. Average length 6¼". Average width 1¾".
- *Texture.*—Smooth.
- *Margin.*—Crenate.
- *Form.*—Lanceolate, pointed.
- *Petiole.*—Medium length. Medium thickness.
- *Glands.*—Number varies from 1 to 3. Average number 2. Reniform. Medium size. Located on lower portion of leaf blade and upper portion of petiole.
- *Color.*—Upper surface—green to dark green (28-E-7) to (28-F-8). Lower surface—grayish green to green (28-E-6) to (28-E-7).

Flower buds:
*Size.*—Medium.
*Form.*—Plump.
*Length.*—Medium.
*Pubescence.*—Pubescent.
Flowers:
*Size.*—Medium, non-showy.
*Pollen.*—Present, self fertile.
*Color.*—Pink.
*Blooming period.*—Date of first bloom: Mar. 5, 1994 Date of last bloom: Mar. 11, 1994. Varies slightly with climatic conditions.
Fruit:
*Maturity when described.*—Firm ripe.
*Date of first picking.*—Jun. 21, 1994.
*Date of last picking.*—Jun. 26, 1994.
*Size.*—Large. Average diameter axially 3⅛". Average transversely in suture plane 3³⁄₁₆".
*Form.*—Globose, nearly symmetrical, slightly flattened on stem end. *Suture.*—Shallow, extends from base to apex.
*Ventral surface.*—Nearly round, some fruit very slightly lipped.
*Apex.*—Usually slight pistil point, varies from slight point to retuse.
*Base.*—Retuse.
*Cavity.*—Round to slightly elongated in suture plane. Average depth ½". Average breadth 1".
Flesh:
*Texture.*—Firm
*Juice.*—Moderate.
*Ripens.*—Evenly.
*Aroma.*—Moderate.
*Fibers.*—Few, small, tender.
*Flavor.*—Excellent, mild, subacid, sweet.
*Eating quality.*—Excellent.
*Amygdalin.*—Undetected.
*Color.*—White to slight pinkish white (6-A-l ) to (6-A-2). Pit cavity, light red to geranium red (11-A-6) to (11-A-8), slight bleeding of red into flesh around pit cavity.
Skin:
*Thickness.*—Medium.
*Texture.*—Medium, tenacious to flesh.
*Tendency to crack.*—None.
*Down.*—Moderte amount. Short in length.
*Color.*—White to pinkish white ground color (9-A-1) to (9-A-2). Overspread with red to deep red (10-C-8) to (10-D-8).
Stone:
*type.*—Freestone.
*Size.*—Large. Average length 1½". Average width 1". Average thickness ⅝".
*Form.*—Ovoid to obovoid.
*Base.*—Varies from straight to rounded.
*Sides.*—Mostly equal, varies from equal to unequal.
*Apex.*—Acuminate.
*Surface.*—Pitted throughout, pits vary from round to elongated. Irregularly furrowed toward apex.
*Tendency to split.*—Very slight.
*Color.*—Light brown to reddish brown (8-C-5) to (8-D-6).
Use: Dessert.
*Market.*—local and long distance.
Shipping quality: Good.
Storage quality: Good.

The present new variety of peach tree, its flowers, foliage and fruit herein described may vary in slight detail due to climate, soil conditions and cultural practices under which the variety may be grown; the present description is that of the variety grown under the ecological conditions-prevailing near Modesto, Calif.

We claim:

1. A new and distinct variety of peach tree, substantially as illustrated and described, characterized by its large size, vigorous, upright growth and a regular and productive bearer of large, firm, white flesh, freestone fruit with a mild, subacid, sweet flavor with excellent eating quality; the fruit is further characterized by having good handling and shipping quality, being nearly overspread with an attractive red skin color and maturing approximately 10 days after White Lady Peach (U.S. Plant Pat. No. 5821).

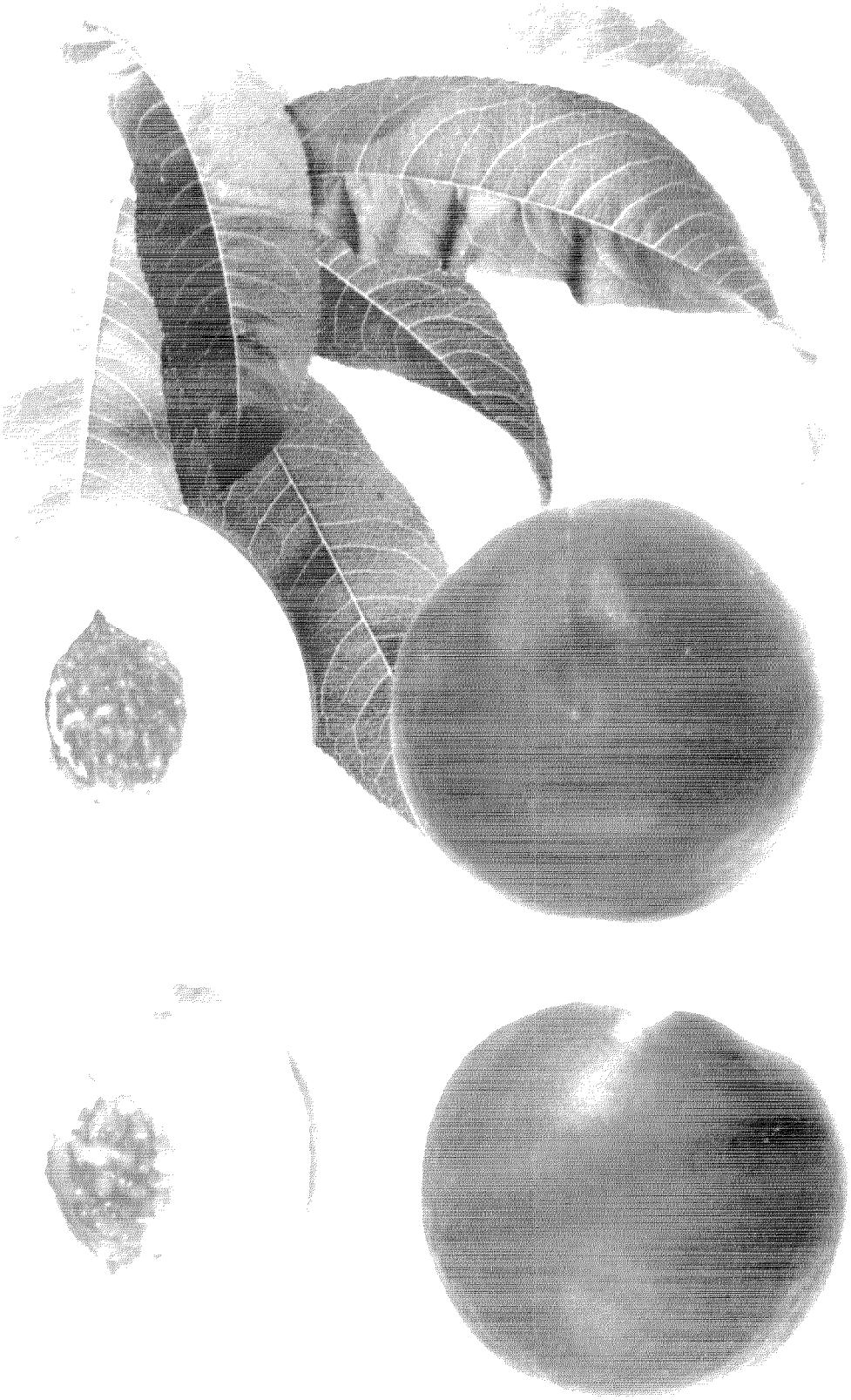

* * * * *